United States Patent
Vijay

(10) Patent No.: US 7,458,952 B2
(45) Date of Patent: Dec. 2, 2008

(54) INTEGRATED CARDIOPULMONARY BYPASS SYSTEM FOR OPEN AND CLOSED BYPASS CIRCUITS

(76) Inventor: Venkataramana Vijay, 624 Jefferson Blvd., Fishkill, NY (US) 12524

( * ) Notice: Subject to any disclaimer, the term of this patent is extended or adjusted under 35 U.S.C. 154(b) by 111 days.

(21) Appl. No.: 11/273,626

(22) Filed: Nov. 14, 2005

(65) Prior Publication Data
US 2006/0155237 A1 Jul. 13, 2006

Related U.S. Application Data

(60) Provisional application No. 60/635,113, filed on Nov. 18, 2004.

(51) Int. Cl.
*A61M 37/00* (2006.01)
*A61M 1/00* (2006.01)
(52) U.S. Cl. .............. 604/6.1; 604/4.01; 604/5.01; 604/6.13; 604/6.14; 604/6.11; 422/44; 422/45; 422/46; 422/47
(58) Field of Classification Search ............ 604/4.01, 604/6.07, 6.09, 7, 5.01, 6.01, 6.1–6.14, 6.16, 604/65, 67, 73, 122, 405, 406; 422/44–48; 210/305, 335, 446, 90, 97, 98, 103, 104; 261/24, 26–30, 82–87, 110
See application file for complete search history.

(56) References Cited

U.S. PATENT DOCUMENTS

| | | | |
|---|---|---|---|
| 4,026,669 | A | 5/1977 | Leonard et al. |
| 4,466,804 | A | 8/1984 | Hino |
| 4,529,397 | A | 7/1985 | Hennemuth et al. |
| 4,850,954 | A | 7/1989 | Charvin |
| 5,011,469 | A | 4/1991 | Buckberg et al. |
| 5,263,924 | A | 11/1993 | Mathewson |
| 5,270,005 | A | 12/1993 | Raible |
| 5,358,481 | A | 10/1994 | Todd et al. |
| 5,766,480 | A | 6/1998 | Cosentino et al. |
| 5,823,986 | A * | 10/1998 | Peterson .................. 604/6.09 |
| 5,879,316 | A | 3/1999 | Safar et al. |
| 6,071,258 | A | 6/2000 | Dalke et al. |
| 6,306,346 | B1 | 10/2001 | Lindsay |
| 6,315,751 | B1 | 11/2001 | Cosgrove et al. |
| 6,344,139 | B1 | 2/2002 | Utterberg |
| 6,443,922 | B1 | 9/2002 | Roberts et al. |

(Continued)

OTHER PUBLICATIONS

K. McCusker et al., "Isolated Extra-Corporeal Coronary Perfusion Circuit for Use During Off-Pump Coronary Artery Bypass Grafting", The Journal of Extra-Corporeal Technology, Sep. 2000, vol. 32, No. 3.

(Continued)

*Primary Examiner*—Leslie Deak
*Assistant Examiner*—Phil Wiest
(74) *Attorney, Agent, or Firm*—Gordon & Jacobson, PC

(57) ABSTRACT

A completely integrated cardiopulmonary bypass system includes a common casing provided with a reservoir, a venous air trap, oxygenator, heat-exchanger and a pump. This totally integrated system provides for volume sequestration and for bypassing the reservoir without use of a shunt. The system also provides for open or closed circuit operation, thereby permitting the volume sequestration. The closed circuit operation has a venous air trap for air removal, thus retaining the safety features of both open reservoir and closed-venous air trap systems.

11 Claims, 4 Drawing Sheets

U.S. PATENT DOCUMENTS

| | | | |
|---|---|---|---|
| 6,468,473 | B1 | 10/2002 | Lindsay |
| 6,506,340 | B1 * | 1/2003 | Tsai et al. .................... 422/45 |
| 6,517,508 | B1 | 2/2003 | Utterberg et al. |
| 6,613,008 | B2 | 9/2003 | Aboul-Hosn et al. |
| 6,632,189 | B1 | 10/2003 | Fallen et al. |
| 6,730,267 | B2 * | 5/2004 | Stringer et al. ................ 422/45 |
| 7,169,303 | B2 * | 1/2007 | Sullivan et al. ........ 210/321.63 |
| 2002/0044889 | A1 | 4/2002 | Aboul-Hosn et al. |
| 2002/0085952 | A1 | 7/2002 | Ellingboe et al. |
| 2002/0087107 | A1 | 7/2002 | Roberts et al. |
| 2002/0176797 | A1 | 11/2002 | Roberts et al. |
| 2003/0204127 | A1 | 10/2003 | Rawles et al. |
| 2003/0208097 | A1 | 11/2003 | Aboul-Hosn et al. |
| 2005/0085762 | A1 * | 4/2005 | Vijay et al. ................ 604/6.14 |

OTHER PUBLICATIONS

K. McCusker et al., "MAST System: a New Condensed Cardiopulmonary Bypass Circuit for Adult Cardiac Surgery", Perfusion 2001, No. 16, pp. 447-452.

"Cardiopulmonary Equipment", COBE Cardiovascular Inc., 2001, downloaded Mar. 7, 2003 from web-site www.cobecv.com/cardiopulmonary.htm.

* cited by examiner

US 7,458,952 B2

INTEGRATED CARDIOPULMONARY BYPASS SYSTEM FOR OPEN AND CLOSED BYPASS CIRCUITS

This application claims the benefit of Provisional Application No. 60/635,113, filed Nov. 18, 2004.

BACKGROUND OF THE INVENTION

Currently, cardiopulmonary bypass (CPB) system components such as the reservoir, oxygenator, venous air trap, filters, heat exchanger and the centrifugal pump head are all separate items that are co-mounted in proximity or are partially integrated for convenience, efficiency and also to decrease prime volume thereby reducing contact surface area and systemic inflammatory response.

The Terumo Mini-X Reduced Prime Perfusion Circuit is a 'co-mounted' bypass system including a reservoir, oxygenator and pump head which are separate units co-mounted and held together by a bracket in close proximity. Another example of a co-mounted system is the Medtronic Resting Heart System.

The Cobe Ideal Mini-Bypass system is a semi-integrated system including an oxygenator, heat exchanger, venous air trap and centrifugal pump head encased in a single unit. The units of a semi-integrated system are generally not individually separable, except for the centrifugal pump head. Another semi-integrated system is the CardioVention CORx® System. These systems do not have an integrated reservoir.

U.S. Pat. No. 6,613,008 to Aboul-Hosn describes a substantially integrated system having a reservoir, oxygenator, heat exchanger, and centrifugal pump head cased in a single unit. However, the system does not include a venous air trap, cannot run as both open and closed systems (i.e., where the blood is open to the atmosphere and where the blood is closed from atmospheric contact), and cannot be used for blood volume sequestration.

Blood volume sequestration is defined as storage of blood pulled from the circuit, whereby such stored blood is no longer in continuity with the circuit blood flow path and/or no longer in constant contact with the circulating blood volume. This is in contrast to conventional blood storage in the reservoir during the procedure, where the so-called 'stored' blood volume is actually continuously being drained and replenished, as it is in fluid continuity with the blood flow path in the circuit and/or constantly in contact with the circulating volume.

In addition, for volume sequestration during the case, it has previously been required to use an external shunt line to bypass the reservoir. Volume sequestration using an external shunt line is disclosed in U.S. Ser. No. 10/403,567, filed Mar. 31, 2003, which is hereby incorporated by reference herein in its entirety.

An integrated system with inseparable components should not sacrifice the flexibility and safety associated with dismantlable systems such as ability to run an open or closed circuit, store/sequester volume and have an effective venous air trap to remove air while operating as a closed system that bypasses the reservoir.

Further, there is no currently known system which fully integrates a reservoir, venous-side air trap (venous air trap), a centrifugal head, heat exchanger and oxygenator.

SUMMARY OF THE INVENTION

A completely integrated cardiopulmonary bypass system according to the invention includes a common casing provided with a reservoir, a venous air trap, oxygenator, heat-exchanger and a centrifugal head. This totally integrated system provides for volume sequestration and for bypassing the reservoir without use of an external shunt. The system also provides for open or closed circuit operation, thereby permitting the volume sequestration. The closed circuit operation has a venous air trap for air removal, thus retaining the safety features of both open reservoir and closed-venous air trap systems.

DETAILED DESCRIPTION OF THE PREFERRED EMBODIMENTS

Figure 1:
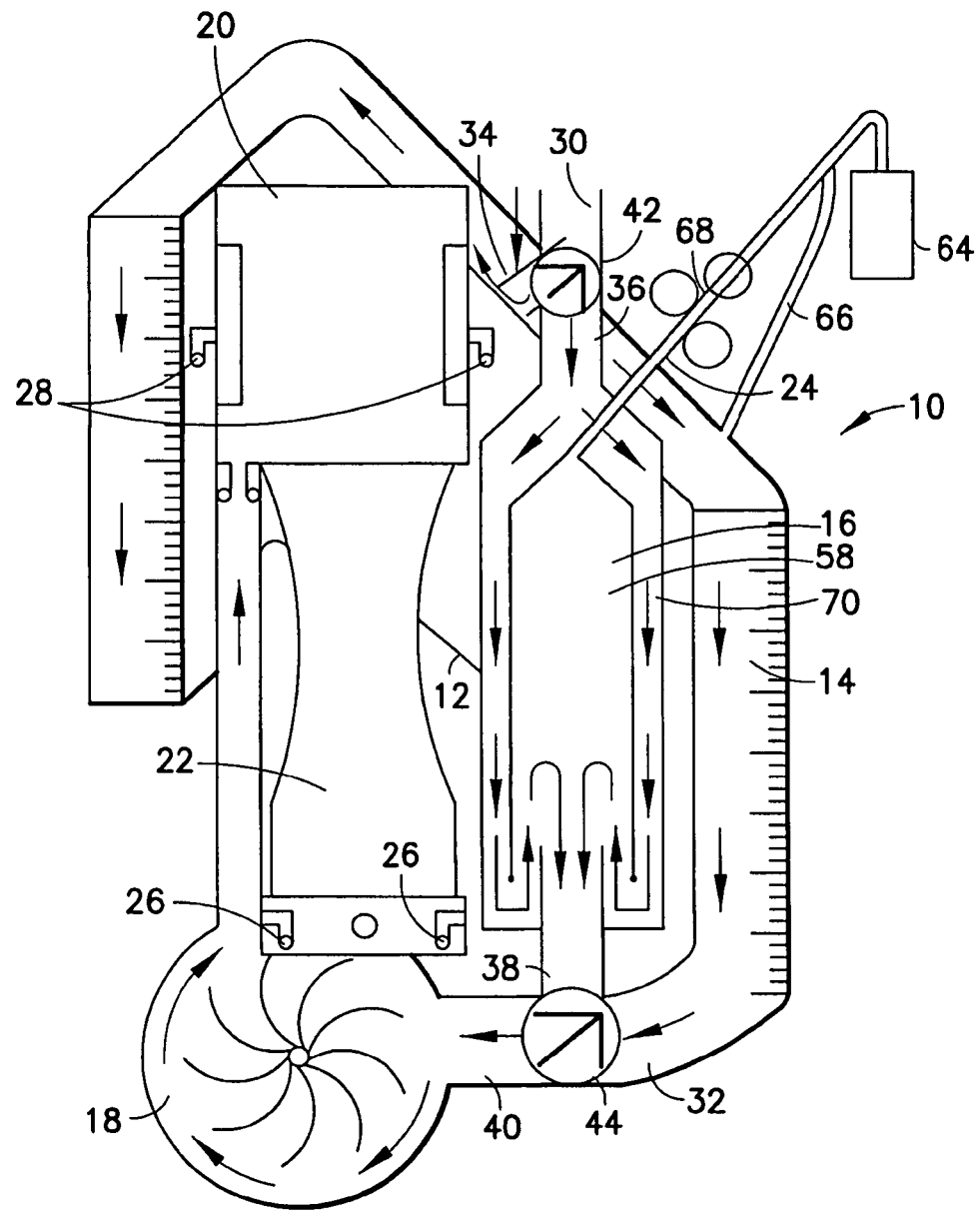
FIG. 1 is a schematic section view through the completely integrated cardiopulmonary bypass system of the invention.

Referring to FIG. 1, a completely integrated cardiopulmonary bypass system 10 includes in a common casing or housing 12 a blood reservoir 14, a venous air trap 16, a centrifugal pump head 18, a heat-exchanger 20 and an oxygenator 22.

The reservoir 14 is preferably a curved unit that encompasses (i.e., substantially surrounds) the venous air trap 16, the pump head 18, the heat exchanger 20 and the oxygenator 22. The capacity of the reservoir 14 is preferably approximately 2.5 to 4 liters. The reservoir 14 forms the back wall of the integrated unit or casing 12, while the front is open to vision and operator access. Particularly, an air evacuation tube 24 (described below) for the venous air trap 16, and various fluid line connectors 26, 28 for the heat exchanger/oxygenator and pump head are visible and accessible.

The reservoir includes an inlet 30, provided for receiving blood from a venous cannula (or other venous-side blood source), and an outlet 32 which directs blood to the pump 18 (and through the bypass system back to an arterial-side blood return, e.g., an arterial cannula). The inlet 30 is a 'Y' connector communicating with the venous cannula at one end and at its other end, it is splayed to directly communicate with the reservoir 14 at a first branch 34 and the venous air trap 16 at a second branch 36.

The outlet 32 from the reservoir 14 communicates with the outlet 38 of the venous air trap 16 and the inlet 40 of the centrifugal pump 18.

At each of the inlet 30 and outlet 32 to the reservoir 14 is stationed a three-way valve 42, 44. The inlet valve 42 directs blood flow when (i) in a first position into the reservoir 14; (ii) in a second position into the venous air trap 16; and (iii) in a third position, to both the reservoir and venous air trap. The outlet valve 44 permits blood flow when (i) in a first position from the reservoir 14; (ii) in a second position from the venous air trap 16; and (iii) in a third position, from both the reservoir and venous air trap. Thus, the system 10 can be used as an open system if the inlet and outlet valves 42, 44 are each in their respective first positions. In addition, the system can be used as a closed system (with no contact between the blood and atmosphere; i.e. excluding the reservoir) by placing the inlet and outlet valves in their respective second positions. When the venous air trap 16 (closed system) pathway is chosen, the reservoir 14 may be used to sequester and store blood volume. Such storage of blood and exclusion of reservoir 14 from the circuit of the system is accomplished without use of an external shunt line. When the closed pathway is in use, any air in the closed circuit can be evacuated via the venous air trap 16. In addition, outlet valve 44 may be placed into the third position, drawing blood from both the reservoir 14 and the venous trap 16, when a closed circuit is being operated and a limited or measured bolus of a sequestrated volume of blood from the reservoir needs to be added to the circulated volume.

The blood volume sequestration may be accomplished by either of two methods. According to a first method, initially inlet valve 42 is turned to the first position which deposits blood into the reservoir 14 and outlet valve 44 is also in its first position. When the desired amount of blood accumulates in the reservoir 14, the inlet valve 42 is then turned to the second position which causes blood to be sent directly to the venous air trap 16, while the outlet valve 44 is also turned to its second position for operation of the closed system.

According to the second method of volume sequestration, volume may be sequestered by turning the inlet valve 42 to its third position, whereby blood is sent to the reservoir 14 as well as the venous air trap 16. After a desired volume of blood has accumulated in the reservoir 14, the inlet valve 42 is changed to its second position for the closed system to operate, and the outlet valve 44 is set to its second position.

Figure 2:
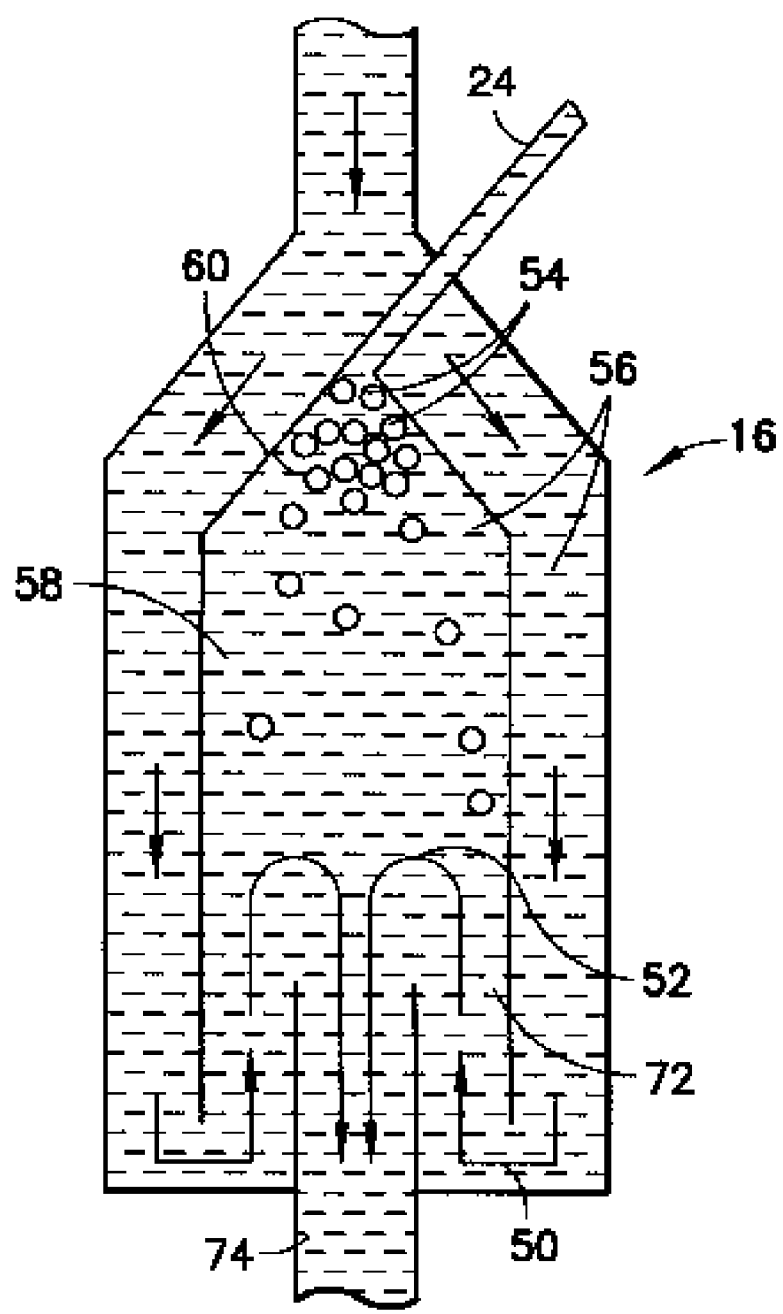
FIG. 2 illustrates the operation of the venous air trap.

Referring to FIGS. 1 and 2, the venous air trap 16 operates on the principle of blood/fluid flow direction reversal, i.e., there is at least one 180° turn (at 50), and preferably two 180° vertical turns (at 50 and 52) in the flow path of the blood fluid which serves to separate air/bubbles 54 from the circulating fluid 56. The venous air trap 16 comprises an air trap chamber 58 which tapers into a dome 60 to trap air. The top of the dome 60 extends into the preferably flexible air evacuation tube 24 that preferably ends in a 'Y' which can be connected to a bag 64 or back to the reservoir at 66. The tube 24 may be passed through a roller pump 68 to develop suction force to draw air collected in the dome 60 of the air trap chamber 58.

This air trap chamber 58 is enclosed in a similarly shaped but slightly larger bulb 70 that receives blood flow from the venous cannula inserted into the heart. Blood flows down to a flow reversal portion 72 of the chamber, i.e., (blood flows down exteriorly, on the sides of the air trap chamber). Blood flow is then reversed in the air trap chamber 58, and air/bubbles 54 rise to the dome 60 of the air trap chamber, while blood is sucked out of the chamber through a bottom port 74, through the outlet valve 44 and into the inlet 40 of the centrifugal pump 18. As the blood level in the chamber 58 is always maintained above the level of the exit port 74, there is no danger of drawing air into the exit port via the air evacuation tube. Further, it is noted that the air evacuation tube 24 is not open to atmosphere.

Figure 3:
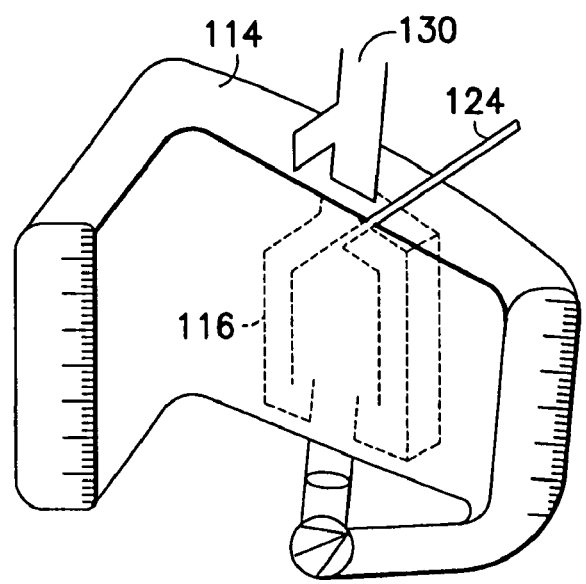
FIG. 3 is a perspective view of an alternate embodiment of the venous air trap relative to the blood reservoir.

Turning now to FIG. 3, in a first alternate embodiment, the venous air trap 116 is provided internal of the reservoir 114, with a bypass of the reservoir occurring within the physical space of the reservoir. As previously incorporated U.S. Ser. No. 10/403,567 suggests, a "shunt" is a passive conduit external to the reservoir having a length of 12 to 18 inches, a ⅜ inch diameter and of prime volume of 20 to 30 cc. In the present embodiment, blood is "shunted" from the venous cannula input 130 through the air trap 116, which is situated within the reservoir. The air trap 116 is an active air removal system (coupled to a siphon pump via evacuation tube 124), is preferably less than 12 to 18 inches length, and has a diameter in the range of preferably approximately 3 to 4 inches. The prime volume is preferably 20 to 100 cc.

Figure 4:
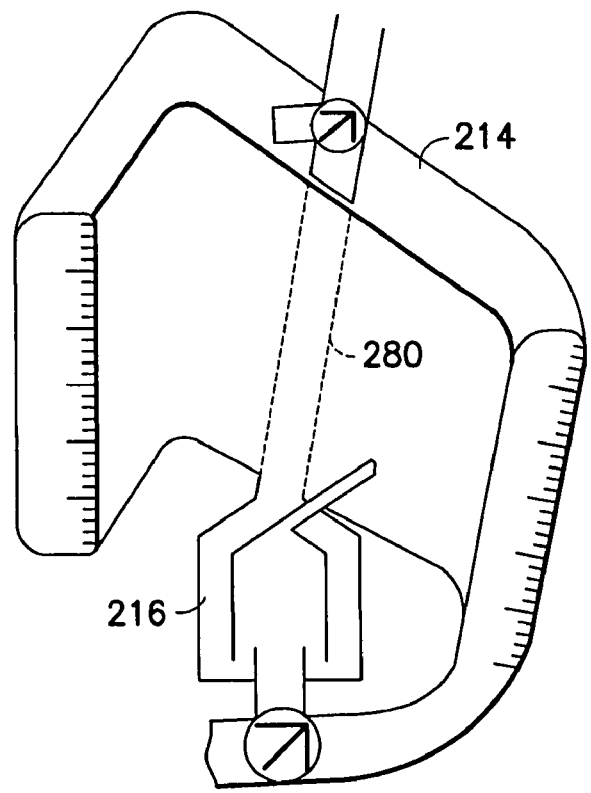
FIG. 4 is a perspective view of another embodiment of the venous air trap relative to the blood reservoir.

Referring to FIG. 4, in a second alternate embodiment, the air trap 216 is external of the reservoir 214 (as in the original embodiment described above), but with a passive conduit ("shunt") 280 located within the reservoir 214 of dimensions which may be substantially as described above, or similar to the shunt in previously incorporated U.S. Ser. No. 10/403, 567, or different in dimension and construct from any previously described. The air trap 216 is preferably provided at the exit end of the passive conduit 280.

Figure 5:
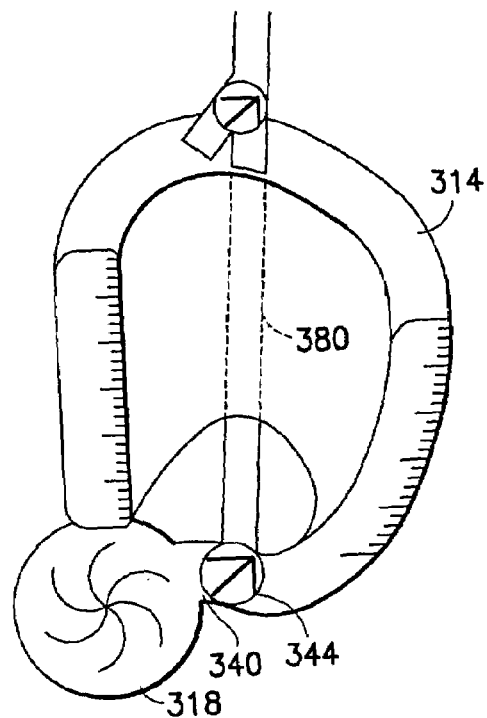
FIG. 5 is a perspective view of an embodiment of the blood reservoir with an internal shunt, both coupled to a centrifugal head pump.

Turning to FIG. 5, in a third embodiment similar to the embodiment shown in FIG. 4, the venous air trap is eliminated. The system includes a curved reservoir 314 with an internal passive conduit 380 that serves as the 'shunt' in the closed system. When air enters the closed system, two options are available. The inlet tube 340 to the centrifugal pump 318 is clamped closed, and the outlet valve 344 is turned to the second position permitting air to be burped into the reservoir 314. Another option is to turn the outlet valve 344 to the third position, and also burping air into the reservoir.

Figure 6:
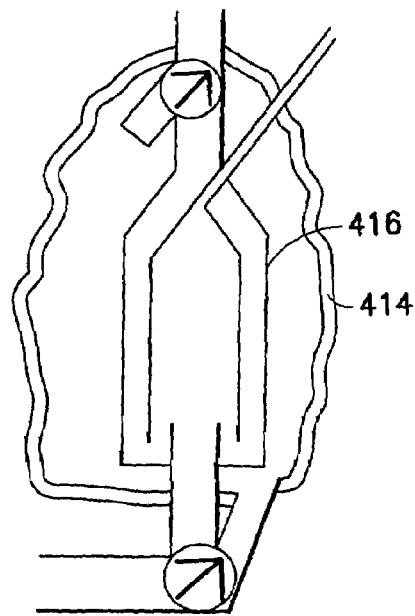
FIG. 6 is a schematic view of an embodiment of a venous air trap and blood reservoir, in which the blood reservoir is collapsible.
Figure 7:
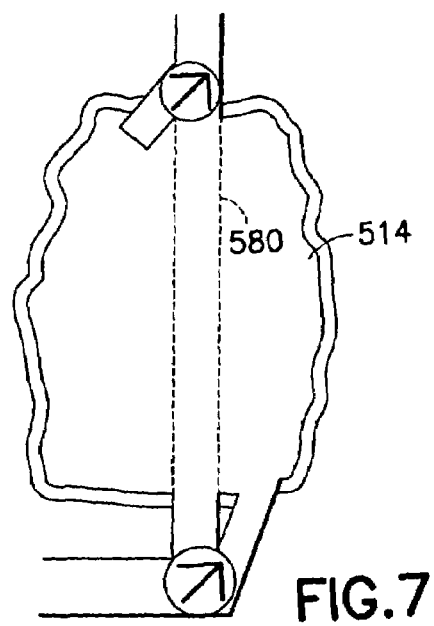
FIG. 7 is a schematic view of an embodiment of the blood reservoir with an internal shunt, in which the blood reservoir is collapsible.

Referring now to FIG. 6, another embodiment of a reservoir 414 and venous air trap 416 is shown. In distinction from the prior embodiment, the reservoir 414 is a soft collapsible bag which is preferably wrapped around the heat exchanger/oxygenator for compactness. As volume is sequestered, the bag 414 expands to capacity and at the same time permits evacuation of air in the same manner as a hard shell reservoir. Then, as blood volume is withdrawn from the bag, the bag collapses, thus preventing any accumulation of air, since dead space is eliminated. Using a collapsible bag, the prime volume of the reservoir can be eliminated entirely. FIG. 7 illustrates an embodiment similar to FIG. 5 (no venous air trap) with a collapsible reservoir 514 and a passive internal conduit 580 extending therethrough. It is recognized that in a closed system with a collapsible reservoir, there is greatly reduced opportunity for air to inadvertently enter the system.

Depending upon the embodiment chosen, the shape of the reservoir may be altered to make the unit more compact. Mirror image or other permutation and combinations of component locations within the unit may also be tried, but the principles of open and closed systems with volume sequestration and venous air removal remain applicable to all the embodiments.

The prime volume of the system 10 is preferably approximately 350 to 500 cc for the rigid reservoir embodiments and 250 to 500 cc for the collapsible reservoir embodiments, not including the volume for the required tubing to couple the system to the venous and arterial cannulas, which can be designed to not exceed an additional 42 to 50 cc by using one foot lengths of ⅜ inch diameter tubing at each end. More particularly, the rigid reservoir 14, while having a 2.5 to 4 liter capacity, has a prime volume of 100 cc, the venous air trap 16 preferably has a prime volume of 100 cc, the pump head 18 has a prime volume of approximately 50 cc, and the heat exchanger 20 and oxygenator 22 together have a prime volume of approximately 150 cc.

There have been described and illustrated herein several embodiments of integrated reservoir/oxygenator systems for open and closed cardiopulmonary bypass circuits and method of volume sequestration without use of an exterior shunt line. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A cardiopulmonary bypass system for connection to a venous-side blood source and an arterial-side blood return, comprising:
   a reservoir having an inlet in fluid communication with the venous-side blood source, and an outlet with a manually operable valve enabling a perfusionist to control the valve and sequester blood in the reservoir from a remainder of the bypass system;
   a venous air trap having an inlet in fluid communication with the venous-side blood source and an outlet, the venous air trap for removing air entrained within blood from the venous-side blood source passing through the air trap;
   a pump for moving blood from the reservoir toward the arterial side blood return, the pump having an inlet in fluid communication with the outlets of the reservoir and the venous air trap;
   an oxygenator for oxygenating blood from the a venous-side blood source; and
   a heat-exchanger through which the blood is transferred,
      the reservoir, the air trap, the pump, the heat exchanger and the oxygenator all provided in a common housing,
      wherein the inlet of the reservoir defines a 'Y' connector having a first end communicating with the venous-side blood source and a second branched end, a first branch of the branched end communicating with the reservoir, and a second branch of the branched end communicating with the inlet of the air trap, and
      at of each of the inlet and outlet to the reservoir is provided a three-way valve,
      the valve at the inlet of the reservoir directing blood flow when (i) in a first position into the reservoir, (ii) in a second position into the air trap, and (iii) in a third position, to both the reservoir and air trap, and
      the valve at the outlet of the reservoir permitting blood flow when (i) in a first position from the reservoir, (ii) in a second position from the air trap, and (iii) in a third position, from both the reservoir and air trap.

2. A bypass system according to claim 1, wherein:
the reservoir substantially surrounds the air trap, the pump, the heat exchanger and the oxygenator.

3. A bypass system according to claim 1, wherein:
the air trap is substantially completely located within the reservoir.

4. A bypass system according to claim 1, wherein:
the air trap causes the direction of the flow of blood to reverse.

5. A bypass system according to claim 4, wherein:
the air trap includes two 180° changes in direction in the flow of blood.

6. A bypass system according to claim 1, further comprising:
an active air removal system coupled to said air trap.

7. A cardiopulmonary bypass system for connection to a venous-side blood source and an arterial-side blood return, comprising:
   a reservoir for storing blood, the reservoir having an inlet in fluid communication with the venous-side blood source, and an outlet with a manually operable valve enabling a perfusionist to control the valve and sequester blood in the reservoir from a remainder of the bypass system;
   a venous air trap having an inlet in fluid communication with the venous-side blood source and an outlet, the venous air trap for removing air entrained within blood from the venous-side blood source passing through the air trap;
   a pump for moving blood from the reservoir toward the arterial side blood return, the pump having an inlet in fluid communication with the outlets of the reservoir and the venous air trap;
   an oxygenator for oxygenating blood from the venous-side blood source;
   a heat-exchanger through which the blood is transferred;
      a first three-way valve is provided communicating the inlet of the venous-side blood source, the inlet of the reservoir, and the inlet of the air trap, and;
      a second three-way valve is provided communicating the outlet of the reservoir, the outlet of the air trap, and the inlet of the pump, wherein
      the first valve directs blood flow when (i) in a first position into the reservoir, (ii) in a second position into the air trap, and (iii) in a third position, to both the reservoir and air trap, and
      the second valve permits blood flow when (i) in a first position from the reservoir, (ii) in a second position from the air trap, and (iii) in a third position, from both the reservoir and air trap.

8. A bypass system according to claim 7, further comprising:
an active air removal system coupled to said air trap.

9. A cardiopulmonary bypass system for connection to a venous-side blood source and an arterial-side blood return, comprising:
   a reservoir for storing blood, the reservoir having an inlet in fluid communication with the venous-side blood source, and an outlet with a manually operable valve enabling a perfusionist to control the valve and sequester blood in the reservoir from a remainder of the bypass system;
   a pump for moving blood from the reservoir toward the arterial side blood return, the pump having an inlet in fluid communication with the outlet of the reservoir;
   a shunt extending through the reservoir and in fluid communication between the venous-side blood source and the pump such that the reservoir can be bypassed;
   an oxygenator for oxygenating blood from the venous-side blood source; and
   a heat-exchanger through which the blood is transferred.

10. A bypass system according to claim 9, wherein:
said reservoir is a constructed of a collapsible material.

11. A bypass system according to claim 9, wherein:
said reservoir is a constructed of a rigid material.

* * * * *